United States Patent [19]

Schreurs

[11] Patent Number: 5,036,843

[45] Date of Patent: Aug. 6, 1991

[54] BREATHING VALVE

[75] Inventor: Albert W. Schreurs, Leiden, Netherlands

[73] Assignee: Mijnhardt B. V., Netherlands

[21] Appl. No.: 446,176

[22] Filed: Dec. 5, 1989

[30] Foreign Application Priority Data

Dec. 29, 1988 [NL] Netherlands ............... 8803202

[51] Int. Cl.$^5$ ..................... A62B 9/02; A61B 5/08
[52] U.S. Cl. ..................... 128/205.24; 128/718
[58] Field of Search ............... 128/201.27, 201.28, 128/205.22, 205.24, 206.15, 207.12, 207.16, 718

[56] References Cited

U.S. PATENT DOCUMENTS 3,643,686 2/1972 Koegel .................. 128/205.24
4,259,951 4/1981 Chernack et al. .......... 128/205.24

Primary Examiner—Edgar S. Burr
Assistant Examiner—Kimberly L. Asher
Attorney, Agent, or Firm—Michael N. Meller

[57] ABSTRACT

Valve device intended for use in an apparatus for examining human metabolism processes through analysis of the breathing air, provided with a connection for a patient mouth-piece and a connection for the hose to the apparatus, an inhalation valve which opens as a result of inhalation and an exhalation valve which opens as a result of exhalation wherein the two connections are disposed in line with each other on a substantially cylindrical housing, and wherein the inhalation valve is formed by several valves in the cylinder wall of the housing distributed substantially along the entire periphery thereof. Preferably the valves are formed in a valve ring on the basis of a regular polygon which is made separately and which, in its entirety, is placed in the internal space of the housing.

3 Claims, 1 Drawing Sheet

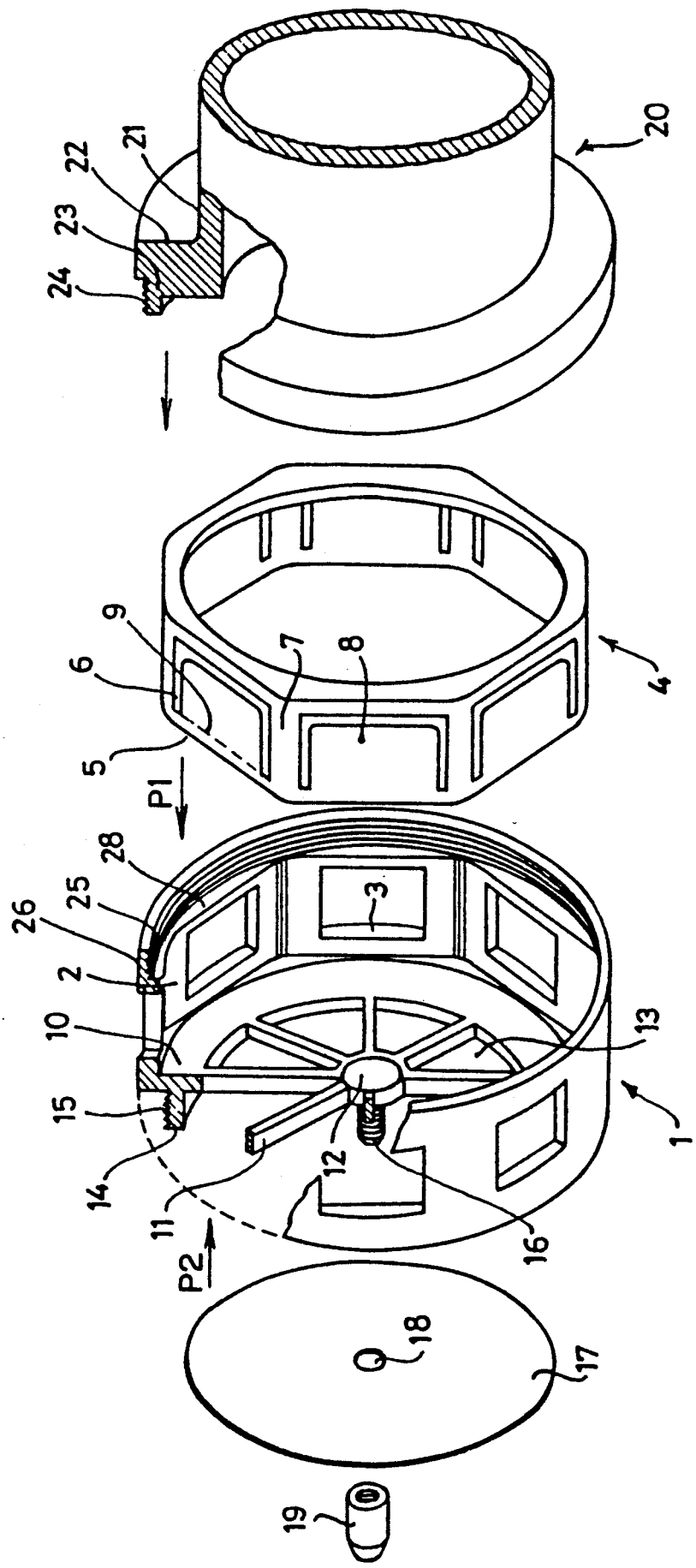

BREATHING VALVE

BACKGROUND OF THE INVENTION

The invention relates to a valve device intended for use in an apparatus for examining human metabolism processes through analysis of the breathing air, said valve device being provided with a connection for a patient mouth-piece and a connection for the connecting hose to the apparatus, and also having an inhalation valve which is placed in such a way that it opens through underpressure or negative pressure as a result of inhalation and admits ambient air, and an exhalation valve which is placed in such a way for the apparatus connection that it opens through excess or positive pressure as a result of exhalation and allows the exhalation air through to the apparatus.

Valve devices of this type in which the housing was in the form of a T-shaped pipe section were used hitherto. The connection for the patient mouthpiece was formed by the body of the T, while the crossbar of the T contained the inhalation valve at one side and the exhalation valve at the other, and the apparatus connection was, of course, also fitted at that end.

This existing valve device had two major disadvantages. In the first place, the total weight was quite high, so that it had to be supported. Secondly, it formed a considerable dead space, which meant that the results of the analysis were affected, or compensation had to be made for them.

THE OBJECTS OF THE INVENTION

The primary object of the invention is to eliminate these two disadvantages. The invention intends to provide a breathing valve of the type which has both a reduced dead space and a reduced weight.

SUMMARY OF THE INVENTION

The device according to the invention is characterized in that the two connections are disposed in line with each other on the ends of an internally and externally, substantially cylindrical housing, and the inhalation valve is formed by several valves in the cylinder wall of the housing distributed substantially along the entire periphery thereof. In this way, the peripheral measurement of the housing is used to determine a dimension of the total valve cross-section, which means that the axial measurement of the whole unit, and thus in particular the dead space, can be kept lower.

A preferred embodiment is characterized in that the valves are formed in a valve ring on the basis of a regular polygon which is made separately and which, in its entirety, is placed in the internal space of the housing. This regular polygon is preferably an octagon, so that eight valves are present. This means that, assuming the necessary structural strength for both the housing and the valve ring, a maximum inlet cross-section of the inhalation valves is obtained, so that the breathing resistance is also kept as low as possible.

The exhalation valve can be a disc with a central fastening which seals against a flat peripheral ring in one of the end faces of the housing.

In an embodiment of the valve device according to the invention used in practice the dead space, which in the device used hitherto was 90 ml, is reduced to no more than 25 ml. At the same time, the whole unit can be made so small and light that it can be accommodated easily between the apparatus hose and the patient mouthpiece, without a separate support. The external center line of the housing, thus in fact the entire valve device, can be equal in size to the external diameter of the apparatus hose. The breathing resistance of the device in this embodiment lies well within the standards which are set for valves on equipment for respiratory analysis.

The invention will be explained below with reference to the drawing of a preferred embodiment.

BRIEF DESCRIPTION OF THE DRAWING

The FIGURE shows an exploded view of the valve device.

DESCRIPTION OF A PREFERRED EMBODIMENT

The housing 1 is externally circular cylindrical and is internally provided with an octagonal chamber 2. An essentially rectangular window is disposed centrally in each of eight flat parts through the entire thickness of the housing; one such window is indicated by 3.

An inlet valve ring 4 has an octagonal cross-section corresponding to that of the chamber 2, while the axial dimension of the ring 4 also corresponds essentially to the axial dimension of the chamber 2, so that it can be placed therein in a direction indicated by the arrow P1. An essentially U-shaped slit 6 is disposed in each flat part 5 of the inlet valve ring 4, in such a way that the legs of the U-shape run parallel to the ribs, 7 of the octagonal ring 4. This produces in each flat part a valve 8 which can bend relative to the connecting line between the end points of the U-shape 6, indicated by the dotted line 9.

The dimensions of the individual valves 8 are slightly larger than the dimensions of the windows 3. When the octagonal valve ring 4 is placed in the chamber 2 of the housing 1, the valves can thus open inwards, something which will, of course, happen when a vacuum relative to the environment is produced in the interior space, while in the presence of excess pressure they will be pressed with their peripheral edges against the peripheral edges of the windows 3, so that the valves then remain closed.

The bottom of the chamber 2 in the housing 1 is formed by a ring 10 connecting to the cylindrical wall of the housing, ten radial ribs 11, and a core piece 12, the parts 10, 11 and 12 lying flush with each other and all being of the same thickness, i.e. their dimension in the axial direction is the same. Apertures 13 are formed between the radial ribs 11.

A peripheral ring 14, provided on the outside with screw thread 15, is also molded on at the outside relative to the flat ring 10. The core piece 12 carries a pin 16 in the center on the outside.

An outlet valve in the form of a round flat disc 17 provided with an axial hole 18 is placed from the outside on the housing 1 in the direction of arrow P2, the hole 18 being pushed over the pin 16. The external center line of the disc 17 is slightly smaller than the internal center line of the cylindrical ring 14 molded on the housing, but is not smaller than the flat ring 10. The valve disc 17 thus comes to rest against the outside of the ring 10, the radial ribs 11 and the core piece 12. In this position the valve disc 17 can be fixed with a retaining nut 19 which can be pushed tightly onto the central pin 16 or can possibly be made on a screw-on nut.

In this way, in the presence of underpressure in the interior, the valve disc 17 will be pressed along the periphery against the flat ring 10, so that it is shut, while in the presence of excess pressure in the interior it will come away with its periphery from the contact with the flat ring 10, and will allow air out into the annular space between its periphery and the inner periphery of the cylindrical ring 14.

The external screw thread 15 can be used for fixing a cap nut thereon, in a manner known per se, for the connection of the hose going to the analysis apparatus.

At the other side there is also a connecting piece 20, on which the patient mouthpiece can be pushed, in a manner which is also known per se. This connecting piece 20 is formed by a short pipe section 21 with a radially outward running flange 22, which is in turn again provided with a short cylindrical ring 23 with external screw thread 24. The screw thread is intended for mating with the internal screw thread 25 at the end edge 26 of the housing 1.

The cylindrical part 21 of the connecting piece 20 preferably has such a center line that a conventional patient mouthpiece made of flexible plastic can be pushed onto it without further adaptation.

It will also be clear that screwing the connecting piece 20 tight relative to the housing 1 leads to the valve ring being confined in the chamber 2 in the housing.

Any elastic material which is suitable for use as a valve can be used for the parts 4 and 17. The housing 1 and the connecting piece 20 can be made as moldings from a more rigid plastic.

The dead space of the valve device according to the invention is formed only by the internal volume of the chamber 2 after the inlet valve ring 4 is placed therein. Said dead space is bounded physically at one side by the inward-facing face of the outlet valve 17 and at the other side by the imaginary end face of the housing at the side of the connecting piece 20. In an embodiment used in practice, in which the external center line of the housing 1 is 43.5 mm and the axial dimension of the housing 1, including the edge 26 and the ring 14, is 23.0 mm, a dead space of no more than 20 ml is obtained, which thus constitutes a considerable improvement compared with the hitherto used T-shaped valve device which had a dead space of 90 ml.

What is claimed is:

1. A valve device intended for use in an apparatus for examining human metabolism processes through analysis of the breathing air, comprising: a first connection for a patient mouthpiece; a second connection for a connecting hose to the apparatus; an inhalation valve which is placed in such a way that it opens through negative pressure as a result of inhalation and admits ambient air; and an exhalation valvae which is placed in such a way that it opens through positive pressure as a result of exhalation and allows the exhalation air through, said first and second connections being disposed in line with each other on respective ends of a housing, and the inhalation valve being formed by a plurality of valves in a cylindrical wall of the housing distributed substantially along the entire periphery thereof, wherein said plurality of valves are formed in a valve ring on the basis of a regular polygon which is made separately and which, in its entirety, is placed in an internal space of the housing.

2. A device as in claim 1, wherein the regular polygon is an octagon.

3. A device as in claim 1, wherein the exhalation valve is a disc with a central fastening which seals against a flat peripheral ring in an end face of the housing.

* * * * *